United States Patent
Heitmann et al.

(10) Patent No.: US 6,734,317 B2
(45) Date of Patent: May 11, 2004

(54) PROCESS FOR THE PREPARATION OF ALKALI METAL TETRAALKYLALUMINATES AND USE THEREOF

(75) Inventors: Peter Heitmann, Fröndenberg (DE); Thomas Wanke, Werne (DE); Mario Hüttenhofer, Constance (DE)

(73) Assignee: Crompton GmbH, Bergkamen (DE)

( * ) Notice: Subject to any disclaimer, the term of this patent is extended or adjusted under 35 U.S.C. 154(b) by 0 days.

(21) Appl. No.: 10/447,468

(22) Filed: May 27, 2003

(65) Prior Publication Data

US 2003/0233004 A1 Dec. 18, 2003

(30) Foreign Application Priority Data

Jun. 13, 2002 (DE) .......................................... 102 26 360

(51) Int. Cl.$^7$ .............................. C07F 5/06; C25D 3/00
(52) U.S. Cl. ..................... 556/187; 556/190; 205/237
(58) Field of Search ................................ 556/187, 190; 205/237

(56) References Cited

U.S. PATENT DOCUMENTS 3,254,009 A * 5/1966 Ziegler et al. .............. 205/349
3,285,947 A   11/1966 Ziegler et al. .............. 260/448

FOREIGN PATENT DOCUMENTS

EP    1141447    10/2001

OTHER PUBLICATIONS

H. Lehmkuhl und W. Eisenbach (Liebigs Ann. Chem. 705, At pp. 42–53 (1967) Metallorganische Verbindungen, XLVIII.[1] Erdalkali–bis–tetraalkylalanate und bis–tetraathylboranate[2]. Aus dem Max–Planck–Institut fur Kohlenforschun, Mulheim–Ruhr, Eingegangen am 1 Dezember 1996.

Houben–Wayt. Methoden der Organischen Chemie Tubingen 1970. Salzartige Komplexe mit vierzahligen Aluminium durch mehrstufige Reaktionen.

* cited by examiner

Primary Examiner—Porfirio Nazario-Gonzalez
(74) Attorney, Agent, or Firm—Michael P. Dilworth

(57) ABSTRACT

The present invention relates to a process for preparing alkali metal tetraalkylaluminates, in particular potassium tetraethylaluminate, and also to the use of such an aluminate complex in aluminum deposition by electroplating-electrolysis.

13 Claims, No Drawings

PROCESS FOR THE PREPARATION OF ALKALI METAL TETRAALKYLALUMINATES AND USE THEREOF

The present invention relates to a process for preparing alkali metal tetraalkylaluminates, in particular potassium tetraethylaluminate, and also to the use of such an aluminate complex in aluminum deposition by electroplating-electrolysis.

Alkali metal tetraalkylaluminates are used in the aluminizing of base metals. The aluminum layer deposited electrolytically on the base metal protects this against corrosion, and in addition the aluminum layer has in part decorative character.

Aluminizing is possible in principle by various methods. For example, aluminum can be deposited on a substrate electrolytically by fused-salt electrolysis or from solutions. In the case of deposition from a solution, it is necessary to take into account the fact that aluminum itself is very base and is only protected against further oxidation by an oxide layer adhering at the surface. Therefore, anhydrous media in organic solvents must be employed. Aluminum compounds which are suitable for aluminizing that are used are trialkylaluminum compounds, but in particular the complex tetraalkylaluminates which, as salts in the organic solvents, in addition make possible the current density which is required for rapid and uniform electrodeposition.

The use of potassium tetraethylaluminate has proved to be particularly advantageous, since, in addition to good commercial availability, the above-described conditions of the necessary current densities for rapid and uniform electrodeposition can also be achieved.

In the literature, known processes for preparing sodium tetraethylaluminate start from triethylaluminum which is reacted with liquid sodium, sodium tert-butoxide or other sodium alkoxides. In addition, sodium tetraethylaluminate can be produced from ethene and a triethylaluminum-sodium hydride complex (Houben-Weyl, Methoden der organischen Chemie [Methods in organic chemistry], Tubingen 1970, Metallorganische Verbindungen Vol. XIII/4, pages 123–135; Liebigs Ann. Chem. 705 (1967) p. 43).

The methods known in the literature for preparing potassium tetraethylaluminate include the reaction of triethylaluminum with potassium tert-butoxide and a reaction of sodium tetraethylaluminum with potassium chloride or with potassium amalgam (Houben-Weyl, Methoden der organischen Chemie [Methods in organic chemistry], Tubingen 1970, Metallorganische Verbindungen Vol. XIII/4, pages 123–135; Liebigs Ann. Chem. 705 (1967) s. 43) in a similar manner to the reactions for sodium tetraethylaluminate.

The preparation processes of the prior art have some disadvantages.

The direct preparation of the potassium salt has the problem that the product is difficult to isolate and has a strong discoloration.

All preparation routes via amalgams (Na/Hg or K/Hg) are of concern for toxicological reasons alone.

The preparation pathways for $NaAlEt_4$ via elemental liquid sodium also have processing problems due to the use of pyrophoric liquid sodium.

The addition of ethene to NaH·TEA is very problematic with respect to reaction conditions, since the "run away" of the reaction can be prevented only in a narrow temperature window. Furthermore, the preparation is more complex in processing terms owing to the handling of gaseous reactants and the removal of residual NaH·TEA.

The preparation of $KAlEt_4$ starting from KOtBu+TEA likewise has problems: the reaction is performed at high temperatures and $KAlET_4$ is not produced as solid (owing to its high solubility in hydrocarbons and due to formation of complexes), and therefore complex phase separation is necessary. High-boiling paraffins are used as process solvent. The purity has a tendency to be poor.

Thus U.S. Pat. No. 3,285,947 also indicates the problems of synthesizing pure $KAlEt_4$, but proposes as a solution the route via potassium amalgams.

WO 00/32847 (=EP 1 141 447) also describes the use of sodium tetraethylaluminate and/or potassium tetraethylaluminate as constituents of an electrolytic system for depositing aluminum or magnesium onto differing substrates by electroplating. There, however, the synthesis of the sodium tetraethylaluminate is not mentioned and the synthesis of potassium tetraethylaluminate at high temperature is described.

Complexes of sodium fluoride and triethylaluminum in toluene or xylene are usually used as electrolyte. However, because of their disadvantages of nonuniform coating, in particular in the case of edged, angular substrates, these have been overtaken in the interim.

An object of the present invention is a simple and efficient process for preparing alkali metal tetraalkylaluminates, in particular potassium tetraalkylaluminates.

This object is achieved by a process as claimed in claim 1.

The invention relates to a process for preparing alkali metal tetraalkylaluminate, which comprises adding trialkylaluminum to a solution of alkali metal ethoxide in hydrocarbon, alkali metal tetraalkylaluminate being formed.

An advantage of the inventive process is that by adding trialkylaluminum to a solution of alkali metal ethoxide in hydrocarbon the reaction can readily be controlled, which is accompanied, in particular when sodium ethoxide is chosen (in contrast to other alkoxides), by a plurality of advantages in the preparation of sodium tetraethylaluminate:

1. good commercial availability, simple preparability compared with sodium butoxide
2. production of a further commercially utilizable product diethylethoxyaluminum (DEALOX).

The invention further relates to a process for preparing alkali metal tetraalkylaluminates, which comprises reacting the alkali metal tetraalkylaluminate, which is formed in a first above-described process step, with an alkali metal halide in a further process step to form a cation-exchanged alkali metal tetraalkylaluminate.

The preferred inventive process having the additional double decomposition step is described below with the example of preparing potassium tetraethylaluminate, which is not, however, to be considered to be a restriction of the processes claimed and their process steps.

According to a preferred embodiment, sodium ethoxide is reacted with triethylaluminum to form sodium tetraethylaluminate and diethylethoxyaluminum (DEALOX). For this reaction NaOEt in hydrocarbons is charged and triethylaluminum is added. Suitable hydrocarbons are, in particular, heptane and toluene and mixtures thereof. The products are optionally isolated by decanting or filtration. DEALOX is obtained as a utilizable byproduct. This can be purified in principle by distillation or produced as a hydrocarbon solution.

In an additional step, after isolation of the sodium tetraethylaluminumate intermediate, the double decomposition with KCl can be performed in toluene to give potassium tetraethylaluminate.

Then, a formulation for the deposition of aluminum by electroplating-electrolysis can be prepared by adding toluene and triethylaluminum in varying amounts. The double decomposition step and the preparation of formulation step can also be carried out in combination.

The inventive preparation of potassium tetraethylaluminate via sodium tetraethylaluminate using a double decomposition process has a number of advantages compared with known processes:

1. simple process (no complex drying, no liquid—liquid phase separation)
2. tandem production of diethylethoxyaluminum (DEALOX)
3. good control of the reaction (in contrast to NaH·TEA+ ethene) by charging NaOEt and adding triethylaluminum
4. high purity together with very good yield (high yield/avoidance of caking, in particular when toluene/heptane or heptane alone is used as process solvent)
5. ability to set any ratio between $NaAlEt_4$ and $KAlEt_4$ (5–95%) (important for preparing electrolytes)
6. use of inexpensive nontoxic starting materials such as NaOEt and KCl.

The alkali metal cations can be sodium, potassium and rubidium, with the alkali metal tretraalkylaluminate formed in the first process step preferably containing sodium and the alkali metal tetraalkylaluminate formed in the additional second step preferably containing potassium.

Halides which may be used in the context of this invention are fluoride and chloride and bromide, chloride being preferred. The fluorides may have a tendency toward complex formation with certain aluminumalkyles.

Trialkylaluminum compounds which can be used are trimethylaluminum, triethylaluminum, tri-n-propyl- and tri-i-propylaluminum, and also tri-n-butyl- or tri-sec-butylaluminum and mixtures thereof. Preference is given to triethylaluminum.

In the inventive process, the hydrocarbons used in the first process step are preferably heptane, toluene or mixtures thereof. The additional second step is preferably carried out at 50–100° C. in a hydrocarbon, preferably toluene or xylene. The hydrocarbons can be used in pure form or in a mixture.

According to a preferred embodiment, triethylaluminum is reacted with sodium ethoxide to form sodium tetraalkylaluminate which is then converted into potassium tetraalkylaluminate with potassium chloride. The potassium tetraalkylaluminate formed by the process described is distinguished by particularly high purity.

The invention further relates to the use of potassium tetraalkylaluminate prepared by the inventive process for electroplating metallic substrates with aluminum or magnesium. Potassium tetraalkylaluminate can be used in this process in the form of a formulation containing toluene and trialkylaluminum. Preferably, potassium tetraethylaluminate and triethylaluminum are used.

The invention will be described in more detail below with reference to examples, but without restricting it to these.

EXAMPLES

Synthesis of $NaAlEt_4$ (1st Stage)
Procedure:

In a reaction vessel, 10.00 kg of NaOEt, 22.1 kg of Heptane and 9.5 kg of toluene are charged under a protective nitrogen atmosphere. The mixture is heated to an internal temperature of 70° C. with good mixing (suspension). 35.23 kg of triethylaluminum (TEA) are added. The mixture is stirred for a further 1 h at 70° C. In the course of a further hour the mixture is cooled to room temperature. The stirrer is turned off and phase separation allowed to occur. The phases are separated by decanting.

After the first removal of the liquid phase, the reactor contents are repeatedly resuspended with 26.5 kg of hexane and after the solids have settled, the clear phase is decanted.

The suspension is dried in vacuo at <100 mbar and below 40° C.

Care: the solids are pyrophoric!

Synthesis of $KAlEt_4$ (2nd Stage)
Procedure:

The sodium tetraethylaluminate formed in the first stage can remain as deposited reaction product in the reactor after the first stage, about 22 kg are then present, and 50 kg of toluene are added under a protective nitrogen gas atmosphere. No exothermicity should occur.

Then, 9.86 kg of potassium chloride are added to the stirred supension under a nitrogen atmosphere. During the addition, slight heat of reaction may be observed. After addition the mixture is heated to 90° C. and stirred for a further 2 hours. Thereafter the mixture is cooled to room temperature.

Via the bottom outlet, the reactor contents are discharged onto a filter packed with 1.5 kg of Celatom® (filter aid). The yield is between 83% and 90% for the pure potassium tetraethylaluminate. All operations are to be carried out unter an $N_2$ atmosphere.

What is claimed is:

1. A process for preparing alkali metal tetraalkylaluminate which comprises adding trialkylaluminum to a solution of alkali metal ethoxide in hydrocarbon.

2. The process as claimed in claim 1, wherein the alkali metal ethoxide is sodium ethoxide.

3. The process as claimed in claim 1, wherein the trialkylaluminum is triethylaluminum.

4. The process as claimed in claim 1, wherein the hydrocarbon is heptane, toluene or mixtures thereof.

5. The process as claimed in claim 1, wherein, in an additional step, the alkali metal tetraalkylaluminate formed is reacted with alkali metal halide to form a cation-exchanged alkali metal tetraalkylaluminate.

6. The process as claimed in claim 5, wherein the alkali metal halide is potassium chloride.

7. The process as claimed in claim 5, wherein the cation-exchanged alkali metal tetraalkylaluminate is potassium tetraalkylaluminate.

8. The process as claimed in claim 7, wherein the potassium tetraalkylaluminate is potassium tetraethylaluminate.

9. The process as claimed in claim 5, wherein the additional step is carried out in hydrocarbon at 50–100° C.

10. The process as claimed in claim 9, wherein the hydrocarbon is toluene or xylene.

11. A method of aluminizing a metal surface which comprises exposing said surface to a hydrocarbon solution comprising an alkali metal tetraalkylaluminate under electroplating-hydrolysis conditions, said alkali metal tetraalkylaluminate being prepared by adding trialkylaluminum to a solution of alkali metal ethoxide in hydrocarbon.

12. The method as claimed in claim 11, wherein the alkali metal tetraalkylaluminate is potassium tetraalkylaluminate.

13. The method as claimed in claim 12, wherein the potassium tetraalkylaluminate is potassium tetraethylaluminate.

* * * * *